US011669970B2

United States Patent
Linguraru et al.

(10) Patent No.: US 11,669,970 B2
(45) Date of Patent: Jun. 6, 2023

(54) SYSTEM, APPARATUS, AND METHOD FOR DETECTION OF URETEROPELVIC JUNCTION OBSTRUCTION

(71) Applicant: Children's National Medical Center, Washington, DC (US)

(72) Inventors: Marius George Linguraru, Washington, DC (US); Emily S. Blum, Washington, DC (US); Antonio Reyes Porras Perez, Washington, DC (US); Hans G. Pohl, Washington, DC (US)

(73) Assignee: Children's National Medical Center, Washington, DC (US)

( * ) Notice: Subject to any disclaimer, the term of this patent is extended or adjusted under 35 U.S.C. 154(b) by 334 days.

(21) Appl. No.: 16/500,875

(22) PCT Filed: Apr. 9, 2018

(86) PCT No.: PCT/US2018/026726
§ 371 (c)(1),
(2) Date: Oct. 4, 2019

(87) PCT Pub. No.: WO2018/187807
PCT Pub. Date: Oct. 11, 2018

(65) Prior Publication Data
US 2020/0034970 A1 Jan. 30, 2020

Related U.S. Application Data

(60) Provisional application No. 62/483,026, filed on Apr. 7, 2017.

(51) Int. Cl.
*G06T 7/00* (2017.01)
*G16H 30/40* (2018.01)
(Continued)

(52) U.S. Cl.
CPC .......... *G06T 7/0016* (2013.01); *A61B 6/4057* (2013.01); *A61B 6/50* (2013.01);
(Continued)

(58) Field of Classification Search
CPC ......... G06T 7/0016; G06T 2207/20056; G06T 2207/20064; G06T 2207/30084;
(Continued)

(56) References Cited

U.S. PATENT DOCUMENTS

| 2016/0274128 A1* | 9/2016 | Anderberg | G16H 50/20 |
| 2016/0350933 A1* | 12/2016 | Schieke | G06K 9/6281 |
| 2017/0103521 A1* | 4/2017 | Chukka | G06T 7/0012 |

OTHER PUBLICATIONS

Suriyanto et al. "Quantitative means for differentiating renal obstruction by analyzing renography by compartmental modeling of renal fluid flow rate", Nuclear Medicine Communications, vol. 37, No. 9, Sep. 2018. (Year: 2018).*
(Continued)

*Primary Examiner* — Vu Le
*Assistant Examiner* — Julius Chai
(74) *Attorney, Agent, or Firm* — Oblon, McClelland, Maier & Neustadt, L.L.P.

(57) ABSTRACT

Systems, apparatuses, and methods for diagnosing uretero-pelvic junction obstruction. A set of biomarkers may be extracted from each of one or more time-activity curves associated with diuresis renography and/or functional magnetic resonance urography of one or more kidneys of a patient. One or more calculations can be performed based on the set of biomarkers to identify uretero-pelvic junction obstruction and a classification of severity or criticality thereof.

22 Claims, 8 Drawing Sheets

(51) Int. Cl.
  A61B 6/00    (2006.01)
  G06F 18/214  (2023.01)
  G06F 18/241  (2023.01)
  G06F 18/21   (2023.01)
  G06F 18/2411 (2023.01)
  A61B 5/20    (2006.01)
  G06V 10/764  (2022.01)

(52) U.S. Cl.
  CPC .......... *A61B 6/5217* (2013.01); *G06F 18/214* (2023.01); *G06F 18/2193* (2023.01); *G06F 18/241* (2023.01); *G06F 18/2411* (2023.01); *G06V 10/764* (2022.01); *G16H 30/40* (2018.01); *A61B 5/201* (2013.01); *A61B 6/5247* (2013.01); *A61B 2503/045* (2013.01); *G06T 2207/20056* (2013.01); *G06T 2207/20064* (2013.01); *G06T 2207/30084* (2013.01)

(58) Field of Classification Search
  CPC ........ G16H 30/40; A61B 6/4057; A61B 6/50; A61B 6/5217; A61B 6/5247; A61B 5/201; A61B 2503/045; G06K 9/6256; G06K 9/6265; G06K 9/6268; G06K 9/6269
  See application file for complete search history.

(56) References Cited

OTHER PUBLICATIONS

Garcia et al. "RENEX: An Expert System for the interpretation of 99mTc-MAG3 Scans to Detect Renal Obstruction", The Journal of Nuclear Medicine, vol. 47, No. 2, Feb. 2006. (Year: 2006).*

Bao et al., "Key Variables for Interpreting 99mTc-Mercaptoacetyltriglycine Diuretic Scans: Development and Validation of a Predictive Model", AJR Am J Roentgenol, 2011 (Year: 2011).*

Suriyanto et al., "Quantitative means for differentiating renal obstruction by analyzing renography by compartmental modeling of renal fluid flow rate", Nuclear Medicine Communications, vol. 37, No. 9, Sep. 2016 (Year: 2016).*

Chaiwatanarat T, Padhy AK, Bomanji JB, Nimmon CC, Sonmezoglu K, Britton KE. Validation of renal output efficiency as an objective quantitative parameter in the evaluation of upper urinary tract obstruction. J Nucl Med. May 1993;34(5):845-8. PMID: 8478722. (Year: 1993).*

Taylor A, Garcia EV, Binongo JN, Manatunga A, Halkar R, Folks RD, Dubovsky E. Diagnostic performance of an expert system for interpretation of 99mTc MAG3 scans in suspected renal obstruction. J Nucl Med. Feb. 2008;49(2):216-24. doi: 10.2967/jnumed.107.045484. Epub Jan. 16, 2008. PMID: 18199609; PMCID: P (Year: 2008).*

Garcia EV, Taylor A, Folks R, Manatunga D, Halkar R, Savir-Baruch B, Dubovsky E. iRENEX: a clinically informed decision support system for the interpretation of $^{99}$mTc-MAG3 scans to detect renal obstruction. EurJ Nucl Med Mol Imaging. Sep. 2012;39(9):1483-91. doi: 10.1007/s00259-012-2151-7. Epub 2012 (Year: 2012).*

International Search Report and Written Opinion dated Jun. 28, 2018 in PCT/US2018/026726 filed Apr. 9, 2018.

Garcia, E. V. et al., "RENEX: An Expert System for the Interpretation of $^{99m}$Tc-MAG3 Scans to Detect Renal Obstruction," The Journal of Nuclear Medicine, vol. 47, No. 2, Feb. 2006, pp. 320-329.

Suriyanto, et al., "Quantitative means for differentiating renal obstruction by analyzing renography by compartmental modelling of renal fluid flow rate," Nuclear Medicine Communications, vol. 37, No. 9, Sep. 2016, pp. 904-910.

* cited by examiner

SYSTEM, APPARATUS, AND METHOD FOR DETECTION OF URETEROPELVIC JUNCTION OBSTRUCTION

CROSS-REFERENCE TO RELATED APPLICATIONS

The present application claims priority to U.S. Provisional Application No. 62/483,026, filed Apr. 7, 2017, the teaching of which is hereby incorporated by reference in its entirety for all purposes.

STATEMENT REGARDING PRIOR DISCLOSURE BY THE INVENTORS

Aspects of this technology are described in an article "Early Detection of Ureteropelvic Junction Obstruction Using Signal Analysis and Machine Learning: A Dynamic Solution to a Dynamic Problem", published in The Journal of Urology, on Oct. 21, 2017, which is incorporated herein by reference in its entirety.

FIELD

Generally, embodiments of the present disclosure are directed to systems, apparatuses, and methods for detecting ureteropelvic junction obstruction. More specifically, embodiments of the present disclosure involve systems, apparatuses, and methods to diagnose ureteropelvic junction obstruction, including identification of ureteropelvic junction obstruction and determination of a severity or likely severity of ureteropelvic junction obstruction.

BACKGROUND

Hydronephrosis, or neonatal hydronephrosis, is an enlarging of the renal pelvis and/or calyces of the kidney resulting from an obstruction at the ureteropelvic junction, referred to as an ureteropelvic junction obstruction. Obstructions may result from challenges in structural development of the kidney, such as compressed ureters, or from immunological or other conditions, such as kidney stones. In neonates, hydronephrosis may be congenital, the result of structural anomalies during fetal development. Most cases of congenital hydronephrosis, which affects up to 4.5% of all pregnancies, are of low severity. However, the few infants born with Society for Fetal Urology grade 3-4 hydronephrosis routinely undergo postnatal testing, including sonography, contrast voiding cystography, and assessment of renal function and drainage by diuretic renography to identify those with or at risk for compromised renal function. As most renal units with grade 3-4 congenital hydronephrosis have well preserved function despite impaired drainage, it can become difficult to accurately determine when pyeloplasty, or surgical reconstruction of the renal pelvis, is appropriate. Moreover, criteria for proceeding to surgical intervention in ureteropelvic junction obstruction are, generally, not standardized.

SUMMARY

According to one or more embodiments of the present disclosure, a method for diagnosis of a clinically significant renal obstruction in a patient using signal analysis and machine learning is provided. The method can comprise receiving, using processing circuitry, data corresponding to a machine learned set of extracted biomarkers from one or more time-activity curves associated with a renograph of the patient; and generating, using the processing circuitry, a clinical diagnosis based on the machine learned set of extracted biomarkers.

One or more embodiments of the present disclosure can also provide a non-transitory computer-readable storage medium storing computer-readable instructions that, when executed by a computer, cause the computer to perform a method for diagnosis of a clinically significant renal obstruction in a patient using signal analysis and machine learning. The method can comprise receiving, using processing circuitry, data corresponding to a machine learned set of extracted biomarkers from one or more time-activity curves associated with a renograph of the patient; and generating, using the processing circuitry, a clinical diagnosis based on the machine learned set of extracted biomarkers.

A system for classifying ureteropelvic junction obstruction may also be provided according to one or more embodiments of the present disclosure. The system can comprise memory; and a processor operatively connected to the memory, the processing being configured to extract a set of biomarkers from a time-activity curve corresponding to a renograph of a patient, the extracted set of biomarkers corresponding to a predetermined set of machine-learned biomarkers stored in the memory, to determine, based on the extracted set of biomarkers, a probability of critical ureteropelvic junction obstruction for clinical diagnosis of ureteropelvic junction obstruction in the patient, and to output data corresponding to a recommended treatment based on the determined probability of critical ureteropelvic junction obstruction.

One or more embodiments of the present disclosure can also provide a system, a method, and an apparatus to classifying ureteropelvic junction obstruction and/or diagnosis of a clinically significant renal obstruction in a patient using signal analysis and machine learning based on functional magnetic resonance urography.

BRIEF DESCRIPTION OF THE DRAWINGS

The accompanying drawings, which are incorporated in and constitute a part of the specification, are illustrative of one or more embodiments of the present disclosure, and, together with the description, explain various embodiments of the present disclosure. Further, the accompanying drawings have not necessarily been drawn to scale, and any values or dimensions in the accompanying drawings are for illustration purposes only and may or may not represent actual or preferred values or dimensions. Where applicable, some or all selected features may not be illustrated to assist in the description and understanding of underlying features.

DETAILED DESCRIPTION

The description set forth below in connection with the appended drawings is intended as a description of various embodiments of the described subject matter and is not necessarily intended to represent the only embodiment(s). In certain instances, the description includes specific details for the purpose of providing an understanding of the described subject matter. However, it will be apparent to those skilled in the art that embodiments may be practiced without these specific details. In some instances, structures and components may be shown in block diagram form in order to avoid obscuring the concepts of the described subject matter. Wherever possible, the same reference numbers will be used throughout the drawings to refer to the same or the like parts.

Any reference in the specification to "one embodiment" or "an embodiment" means that a particular feature, structure, characteristic, operation, or function described in connection with an embodiment is included in at least one embodiment. Thus, any appearance of the phrases "in one embodiment" or "in an embodiment" in the specification is not necessarily referring to the same embodiment. Further, the particular features, structures, characteristics, operations, or functions may be combined in any suitable manner in one or more embodiments, and it is intended that embodiments of the described subject matter can and do cover modifications and variations of the described embodiments.

It must also be noted that, as used in the specification, appended claims and abstract, the singular forms "a," "an," and "the" include plural referents unless the context clearly dictates otherwise. That is, unless clearly specified otherwise, as used herein the words "a" and "an" and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit embodiments of the described subject matter to any particular orientation or configuration. Furthermore, terms such as "first," "second," "third," etc. merely identify one of a number of portions, components, points of reference, operations and/or functions as described herein, and likewise do not necessarily limit embodiments of the described subject matter to any particular configuration or orientation.

Often, the decision to surgically intervene in patients with ureteropelvic junction obstructions (UPJO) relies heavily on the subjective interpretation of a time-activity curve, a commonly used graphical representation of the relationship of a concentration of a radioactive substance and time, reflecting, as it relates to the kidney, renal function and the ability to produce urine and transport it via the ureters to the bladder. While pyeloplasty, a common surgical approach to UPJO, can be effective, the determination of criticality of the UPJO relies on the above-described subjective, diagnostic approach, an approach impaired by high inter-observer variability. Furthermore, as discussed above, repeated postnatal testing and diuretic renography, in particular, are frequently required in order to longitudinally evaluate renal unit function and determine if and when surgical intervention is appropriate.

The lack of accuracy in time-activity curve evaluation leading to low inter-observer variability can be attributed, in part, to the use of limited metrics in determining renal function. Current approaches in the evaluation of diuretic renographs include the drainage half-time ($t_{1/2}$; time to drain half a radiotracer) of a radiotracer from a kidney after administration of a diuretic, an approach that is a standard tool in the analysis and assessment of ureteropelvic junction obstruction. While commonly used, drainage half-time analysis alone on a diuretic renograph may be insufficient to identify or predict severe or critical obstruction, thus necessitating repeated diuretic renographs for longitudinal evaluation. Similarly, functional magnetic resonance urography, another approach to evaluating renal function and obstruction, is retarded by single-metric analyses that may not be sufficient to identify or predict severe or critical renal obstruction.

In an effort to expand the library of performance metrics, other factors, such as clearance of the radiotracer from the kidney in the upright position (CUP) and percentage of clearance after 30 minutes (C30), have been proposed as additional approaches to evaluate the severity of obstruction. Since congenital hydronephrosis is a dynamic process, however, it is unlikely that a single metric, in isolation, will prove sufficiently robust to identify and predict clinically significant obstruction.

Machine learning approaches, therefore, enable the extraction of a plurality of biomarkers indicative of possible disease states. Specifically, it may be possible to harvest a plurality of dynamic data from the time-activity curves of standard diuretic renographs to generate a more accurate, and potentially more predictive, metric of clinically significant obstruction when compared to current, state-of-the-art, descriptors.

Embodiments of the present disclosure can be directed to diagnosing unilateral and/or bilateral ureteropelvic junction obstruction (UPJO), where UPJO can be identified and assessed to determine a severity, or likely severity, such as critical (e.g., requiring surgery) or non-critical (e.g., not requiring surgery). Generally, such diagnosis is performed based on data from renographs obtained, for instance, through diuretic renography (DR) and/or functional magnetic resonance urography (fMRU). Further, diagnosis according to one or more embodiments of the present disclosure can be performed via a fully- or partially-automatic machine-learning based framework.

In the case of diagnosis via renography, embodiments of the present disclosure can be based on time-activity curve analysis, feature extraction, and classification. Such diagnosing according to one or more embodiments of the present disclosure can provide a more accurate and/or earlier diagnosis as compared to, for instance, a single-metric-based approach (e.g., drainage halftime, $t_{1/2}$, in isolation). Furthermore, the diagnosis can be accurately performed using only a single renograph (e.g., diuretic nuclear renograph), which may prevent or reduce the number of additional renography required to determine whether a patient's UPJO is severe enough to require surgical treatment. Likewise, in one or more embodiments of the present disclosure, diagnosis based on fMRU can be non-invasive and may involve only a single urograph.

Regarding diagnosis of UPJO according to one or more embodiments of the present disclosure, a set of biomarkers may be extracted from each of one or more time-activity curves associated with a DR of one or more kidneys of a patient. One or more calculations can be performed based on the set of biomarkers to identify UPJO and a classification of severity, clinical significance, or criticality thereof. Additionally, the classification may be provided in terms of a probability of severity. Further, as noted above, a classification with respect to severity of a UPJO may be in terms of whether the case requires surgical intervention.

Regarding diagnosis of UPJO using fMRU, according to one or more embodiments of the present disclosure, the analysis can include analyzing signal change over time and subsequent analysis of the curves. Non-limiting examples of analyzed curves include calyceal transit time, renal transit time, and signal intensity time curves. Generally speaking, calyceal transit time can be determined by analyzing signal intensity with respect to time as a contrast agent passes from the renal cortex to the calyces, which may be characterized as a nephron function marker; renal transit time can be determined by analyzing signal intensity with respect to time as the contrast agent passes from the renal cortex to the proximal ureter, and may be used as an evaluation of obstruction; and signal intensity-transit time curves can use the signal intensity of gadolinium, for example, to provide information regarding perfusion, uptake, and excretion, where any asymmetry may suggest or be indicative of differences in function and/or drainage.

Figure 1:
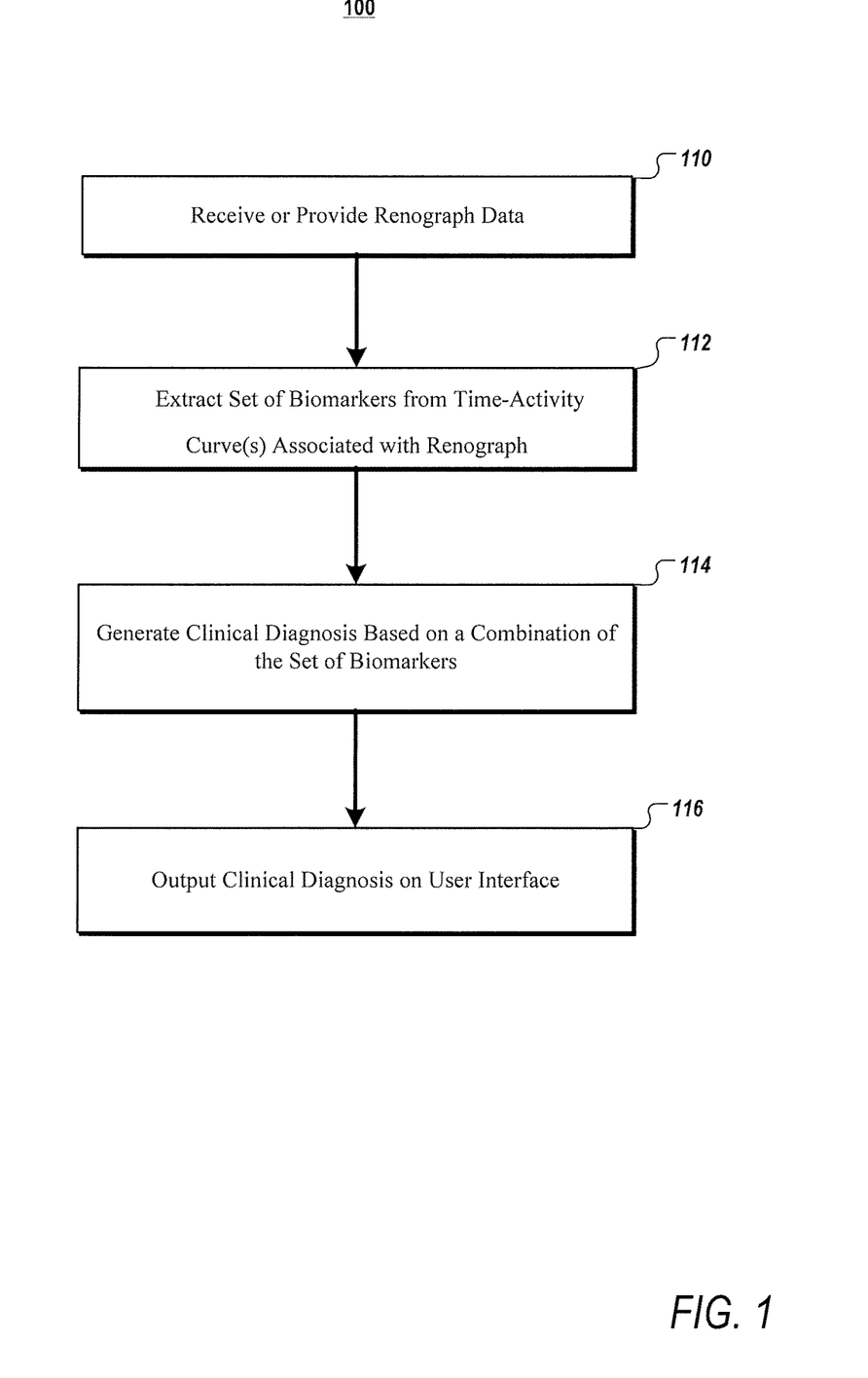
FIG. 1 is a flowchart of a method for diagnosing ureteropelvic junction obstruction according to one or more embodiments of the present disclosure.

Turning now to the figures, FIG. 1, as alluded to above, is a flow chart of a method 100 for diagnosing UPJO. According to one or more embodiments of the present disclosure, the method 100 can identify UPJO, which may be referred to as a clinically significant obstruction, and classify UPJO in terms of severity or significance. The classification of UPJO, which may indicate critical or non-critical, for instance, can form the basis for a clinical diagnosis of UPJO. Further, the clinical diagnosis can be indicative of recommended treatment, such as surgical treatment in a case where the UPJO is classified as critical.

Generally, the method 100 can be performed using a processor or processing circuitry. Further, the method 100 can be implemented by way of the processor or processing circuitry in the form of a general purpose computer having or provided with computer-readable instructions that configure the general purpose computer to perform some or all of the operations of the method 100.

At block 110, the method 100 can include receiving or providing data from a renograph of one or both kidneys as part of DR, for instance, on a patient with hydronephrosis. In an example, the renograph data can be received by accessing a server holding patient information, particularly data corresponding to the renograph(s) of the patient.

Figure 2:
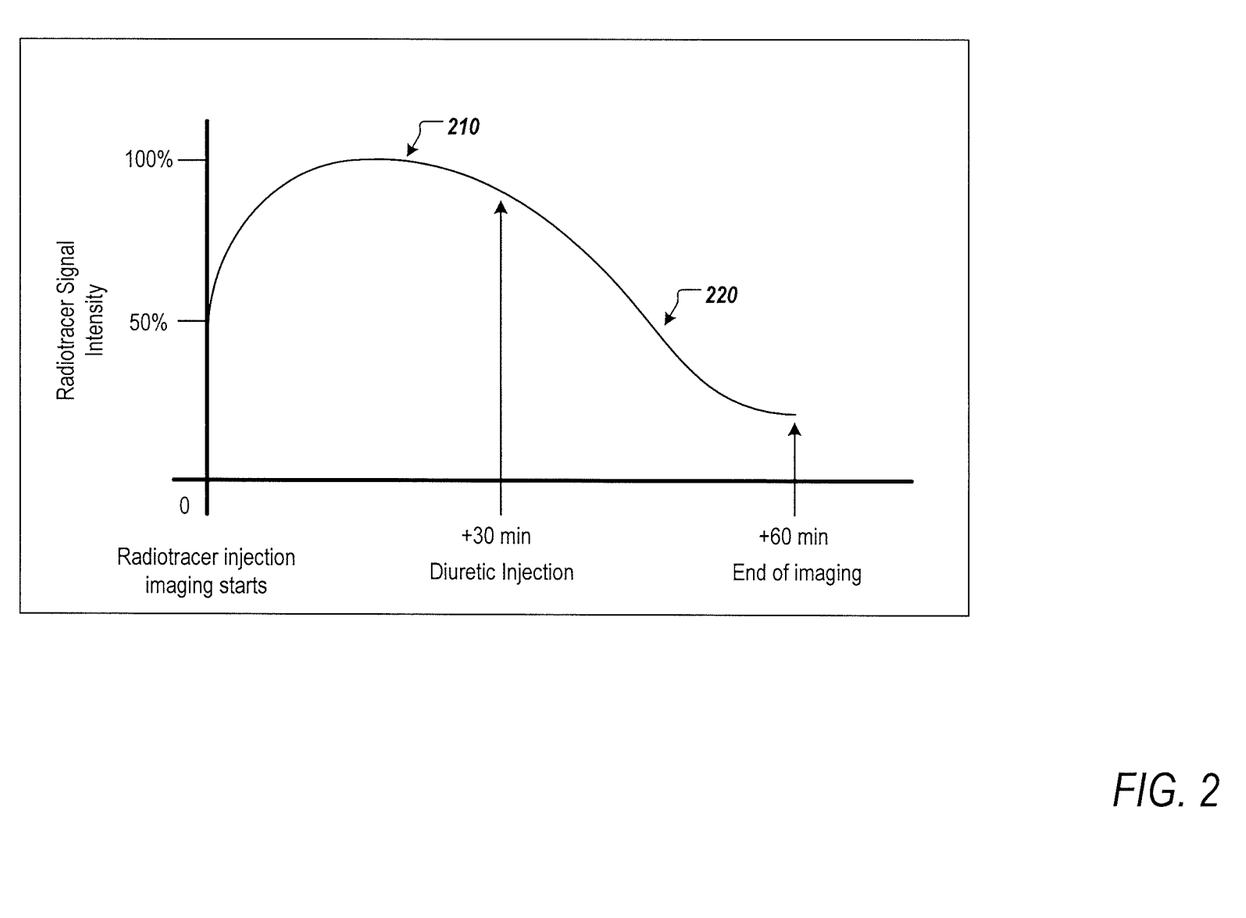
FIG. 2 is an illustration of a stylized time-activity curve, according to one or more embodiments of the present disclosure.

The data can include or be data corresponding to one or more time-activity curves associated with the renograph. FIG. 2 is an illustration of a stylized time-activity curve, where the x-axis represents time and the y-axis represents signal intensity from a delineated kidney at each time point. Generally, at time +0 minutes, a bolus of radiotracer, or contrast agent, is introduced to the patient and imaging of aspects of the kidneys is initiated. Examples of radiotracers include but are not limited to Technetium 99m mercaptoacetyltriglycine and Technetium 99m diethylenetriaminepentacetate. Following +30 minutes, or sufficient accumulation 210 of the radiotracer in the kidneys, a diuretic is administered to the patient. The diuretic can include but is not limited to furosemide. Image acquisition of the radiotracer continues as the kidney is voided of the radiotracer, as indicated by the drop in signal intensity 220 between +30 minutes and +60 minutes from the start of the test. At +60 minutes, or when sufficient radiotracer has been eliminated from the kidney, image acquisition is completed. According to an embodiment, signal intensity of the radiotracer may be correlated with ultrasonic images of the structure of the kidney and may be indicative of structural abnormalities, including dilation.

Figure 3:
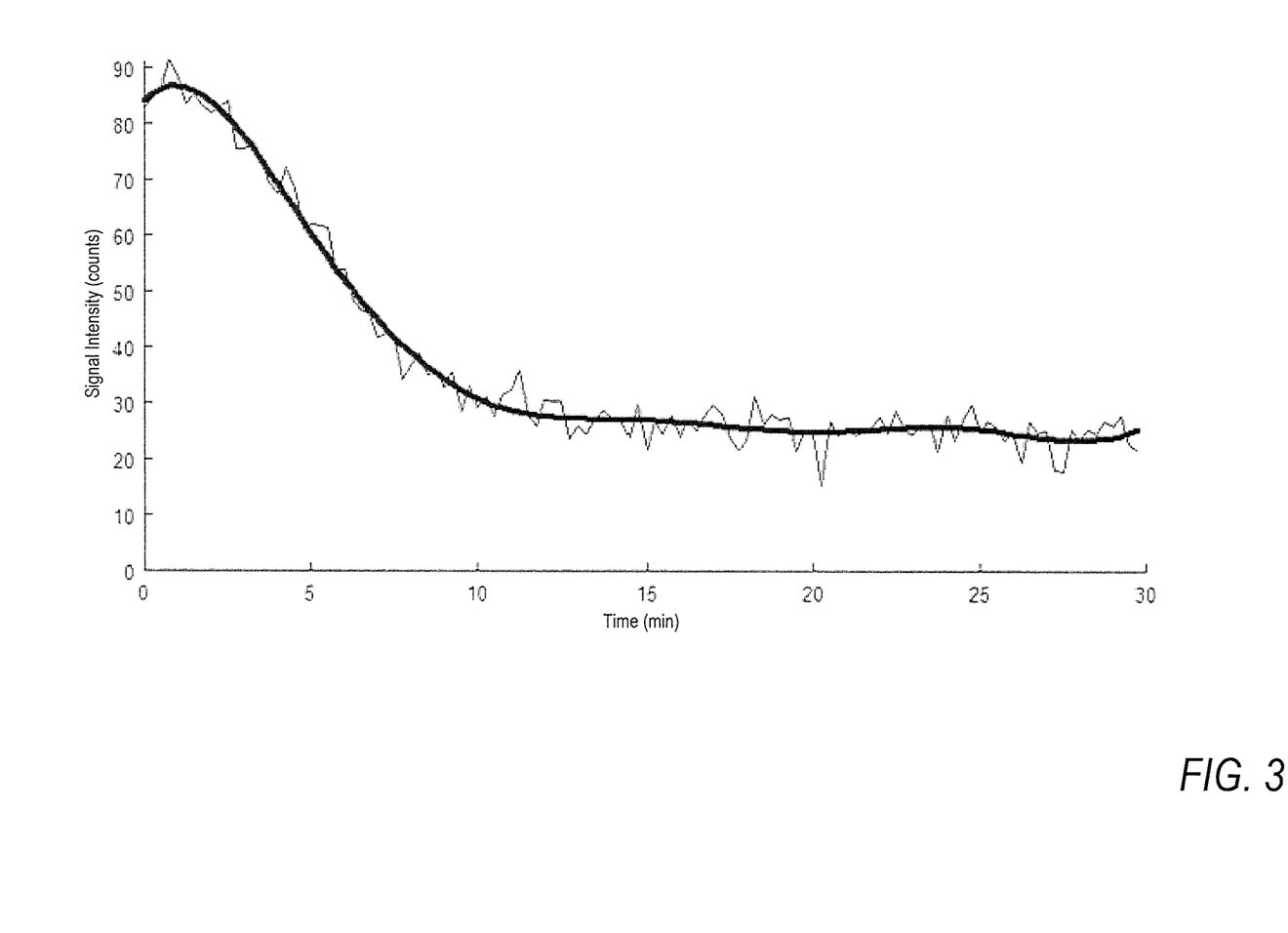
FIG. 3 is a graph showing an example of a time-activity curve (thin line) over time and a noise-minimized time-activity curve (thick line) according to one or more embodiments of the present disclosure.

FIG. 3 illustrates a non-limiting example of a time-activity curve ascertained from the data acquired via radiotracer, where the x-axis represents time and the y-axis represents signal intensity from a delineated kidney at each time point. Generally, a time-activity curve can be fitted to the extracted signal intensities, thus reflecting radiotracer concentration before and after administration of a diuretic. FIG. 3 shows, for instance, a subset of a time-activity curve (see thin line in FIG. 3) sampled over time (e.g. 120 samples) following diuretic administration. Optionally, to minimize the effects of noise, a cubic spline may be fitted to the data from the time-activity curve and used for analysis (see thick line in FIG. 3) Additionally, or alternatively, noise may be further removed or reduced from the time-activity curve by determining a moving average of the extracted signal intensities.

According to an embodiment, the data from the renograph may be the only data received for the method 100. That is, in one or more embodiments of the present disclosure, data from only one renograph of a patient may be used to generate a diagnosis of UPJO. Additionally, or alternatively, in one or more embodiments of the present disclosure, data from only one time-activity curve of the renograph of the patient may be used to generate the diagnosis of UPJO. Of course, data from one or more previous renographs of one or more previous patients may be used to inform and/or control the analysis of the single renograph or time-activity curve of the current patient.

The method 100, at block 112, can include extracting a set of biomarkers from the time-activity curve(s) associated with the renograph(s). Additionally, or alternatively, a method according to one or more embodiments of the present disclosure can extract a set of biomarkers from a functional magnetic resonance urograph.

Generally, the set of biomarkers can be an optimal set of biomarkers chosen from a larger group of biomarkers based on prior analysis of time-activity curves of other patients. The set of biomarkers may have been selected as a combination of biomarkers that maximized an area under a receiver operating characteristics (ROC) curve within a leave-one-out analysis obtained using a linear support vector machine classifier, for instance. That is, the set of biomarkers may be machine-learned by training the classifier to a reference database of prior analyses of time-activity curves of other prior patients (optionally, in one or more embodiments, the current patient may be considered a prior patient).

According to an embodiment, a supervised learning machine learning model, including but not limited to a linear support vector machine classifier, can be trained on a reference database comprising patients with normal renal function and patients diagnosed with congenital hydronephrosis, patients diagnosed with acquired hydronephrosis, or congenital UPJO. Each patient entry in the reference database comprises DR curves. Further, each entry in the reference database is annotated to provide the linear support vector machine with labeled references. In other words, each biomarker of interest is labeled within each DR curve for healthy patients and for diagnosed patients. After training the classifier on each biomarker, and on iterations of combinations of biomarkers, the classifier can be applied to unknown samples and the performance of the trained classifier can be evaluated.

To this end, and in an unrelated example, where the trained classifier produces a probability that a test sample should be classified as a first group instead of a second group, a test sample is determined to have a probability of 0.84, while the threshold for classification is set to 0.8. The test sample, therefore, is classified positively, also matching the true label of the sample (i.e. a true positive). An ROC curve, a graphical plot comparing the true positive rate of the trained classifier and the false positive rate of the trained classifier, illustrates the ability of a diagnostic to properly classify test samples using different thresholds.

According to an embodiment of the present disclosure, for each individual biomarker and for each set of biomarker combinations, discussed above, an ROC curve is evaluated to determine the area under the curve, an indicator of the performance of the classifier. An optimal biomarker or set of biomarkers is selected as the biomarker or set of biomarkers that maximize the area under the ROC curve, indicative of a high level of accuracy of the classifier. The selected optimal biomarker or set of biomarkers, and associated classification threshold, comprise an optimal operation point, and are recorded and implemented in future classifications.

According to an embodiment of the present disclosure, the optimal operation point, comprising the optimal biomarker or set of biomarkers, was selected in order to maximize classification accuracy (the probability of a correct classification). According to another embodiment of the present disclosure, the optimal operation point can be selected in order to maximize specificity (the ability to correctly rule out a diagnosis in a diagnosis free population) or sensitivity (the ability of a test to detect diagnosis in a population of diagnosed individuals).

According to another embodiment, the machine learning model trained above can be an unsupervised learning machine learning model.

According to an embodiment, the larger group of biomarkers may have been extracted based on curve shape of one or more time-activity curves and wavelet analysis of the one or more time-activity curves. Further, the larger group of extracted biomarkers can include a plurality of features including maximum and minimum values, Fourier transform, and wavelet analysis coefficients. The larger group of extracted biomarkers may also comprise commonly used biomarkers including but not limited to $t_{1/2}$, CUP, and C30. As discussed above, the optimal operation point comprises the features that maximize the classification accuracy.

The set of biomarkers can include at least two, or at least three, of a group of metrics including but not limited to a percentage of clearance of a radiotracer from a kidney of the patient after a pre-determined time (e.g., 20 minutes or 30 minutes), half-time ($t_{1/2}$) to drain the radiotracer from the kidney after administration of diuretic, mean slope of the one or more time-activity curves during the first five minutes, mean slope of the one or more time-activity curves during one or more pre-determined time intervals (e.g., 15 to 20 minutes), moment of the one or more time-activity curves of order four (4), and length of the one or more time-activity curves. Moreover, the group of metrics may include but is not limited to a percentage of clearance of a radiotracer from a kidney of the patient after a pre-determined time (e.g., 50 minutes or 60 minutes), mean slope of the one or more time-activity curves during the first five minutes after administration of diuretic, and mean slope of the one or more time-activity curves during one or more pre-determined time intervals (e.g., 45 to 50 minutes).

Figure 4:
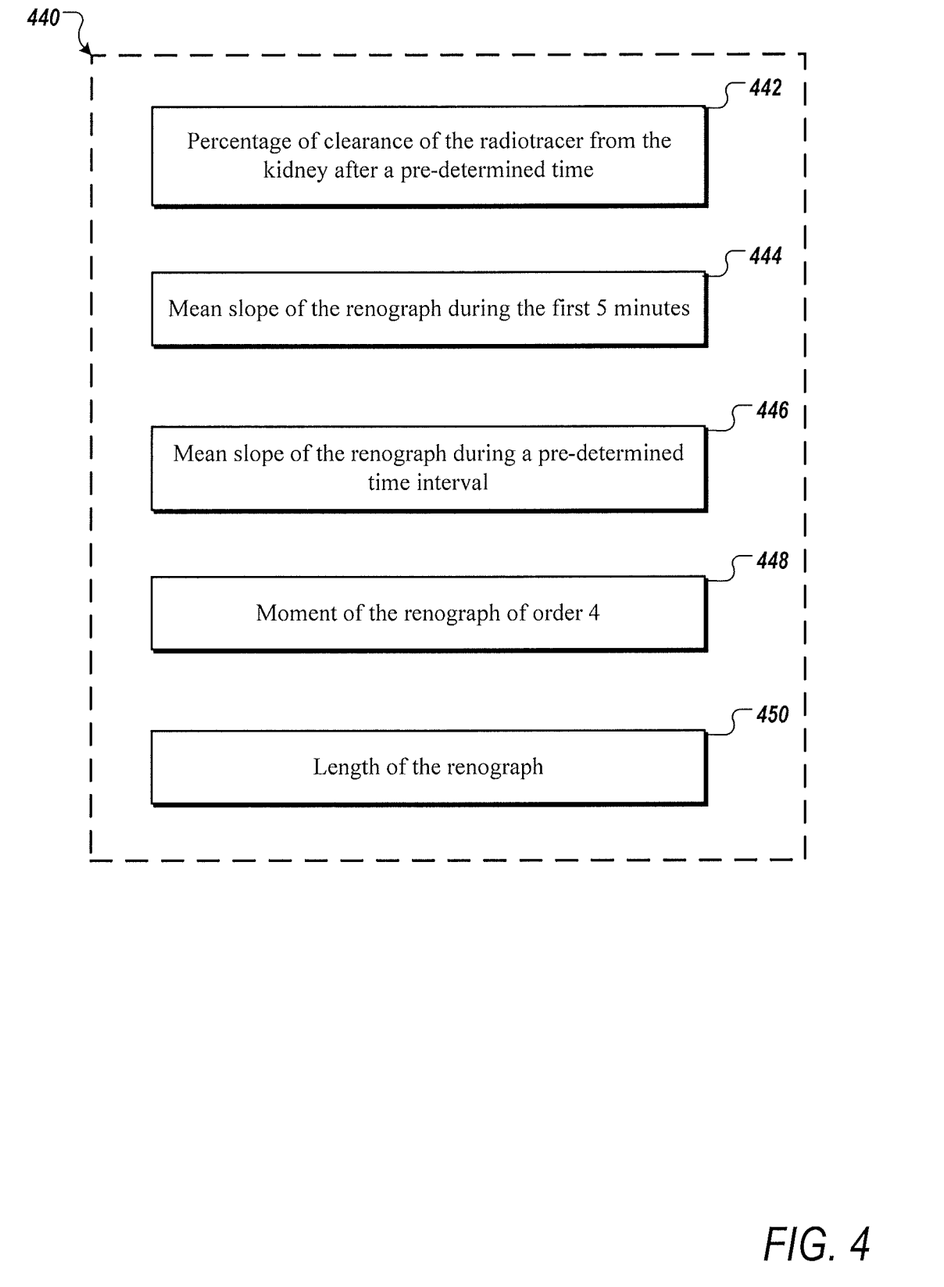
FIG. 4 is an example of an optimized set of biomarkers for extraction from a time-activity curve of a patient.

Optionally, as illustrated in FIG. 4, for instance, in one or more embodiments, the set of biomarkers 440 can consist of a percentage of clearance of a radiotracer from a kidney of the patient after a pre-determined time (e.g., 20 minutes or 30 minutes) 442, mean slope of the one or more time-activity curves during the first five minutes 444, mean slope of the one or more time-activity curves during one or more pre-determined time intervals (e.g., 15 to 20 minutes) 446, moment of the one or more time-activity curves of order four (4) 448, and length of the one or more time-activity curves 450. Moreover, the group of metrics may include but is not limited to a percentage of clearance of a radiotracer from a kidney of the patient after a pre-determined time (e.g., 50 minutes or 60 minutes), mean slope of the one or more time-activity curves during the first five minutes after administration of diuretic, and mean slope of the one or more time-activity curves during one or more pre-determined time intervals (e.g., 45 to 50 minutes). The set of biomarkers can be stored in memory, such as memory 8002 in FIG. 8. Additionally or alternatively, the larger group of biomarkers may be stored in memory, such as the memory 8002 in FIG. 8. Thus, in one or more embodiments, the set of biomarkers may be dynamically selected and set based on the larger group of biomarkers stored in memory.

The method 100, at block 114, can include generating a clinical diagnosis based on the optimized set of extracted biomarkers from block 112.

Block 114 can include generating the clinical diagnosis by subjecting an output signal of a linear support vector machine classifier to a logistic regression function to obtain an approximate probabilistic output corresponding to a probability of a clinically significant renal obstruction representative of part or all of the generated clinical diagnosis. The generated clinical diagnosis can be a probability of a clinically significant renal obstruction, for instance, an approximate probabilistic output generated based on an output of a linear support vector machine classifier processed by a logistic regression function. The clinical diagnosis can be or include a classification of the renal obstruction. Such classification can characterize the obstruction as critical (e.g., requiring surgery) and non-critical (e.g., not requiring surgery). Further, the diagnosis may include recommended treatment. In an example, the diagnosis may recommend pyeloplasty in the case of an obstruction characterized as critical.

Figure 6:
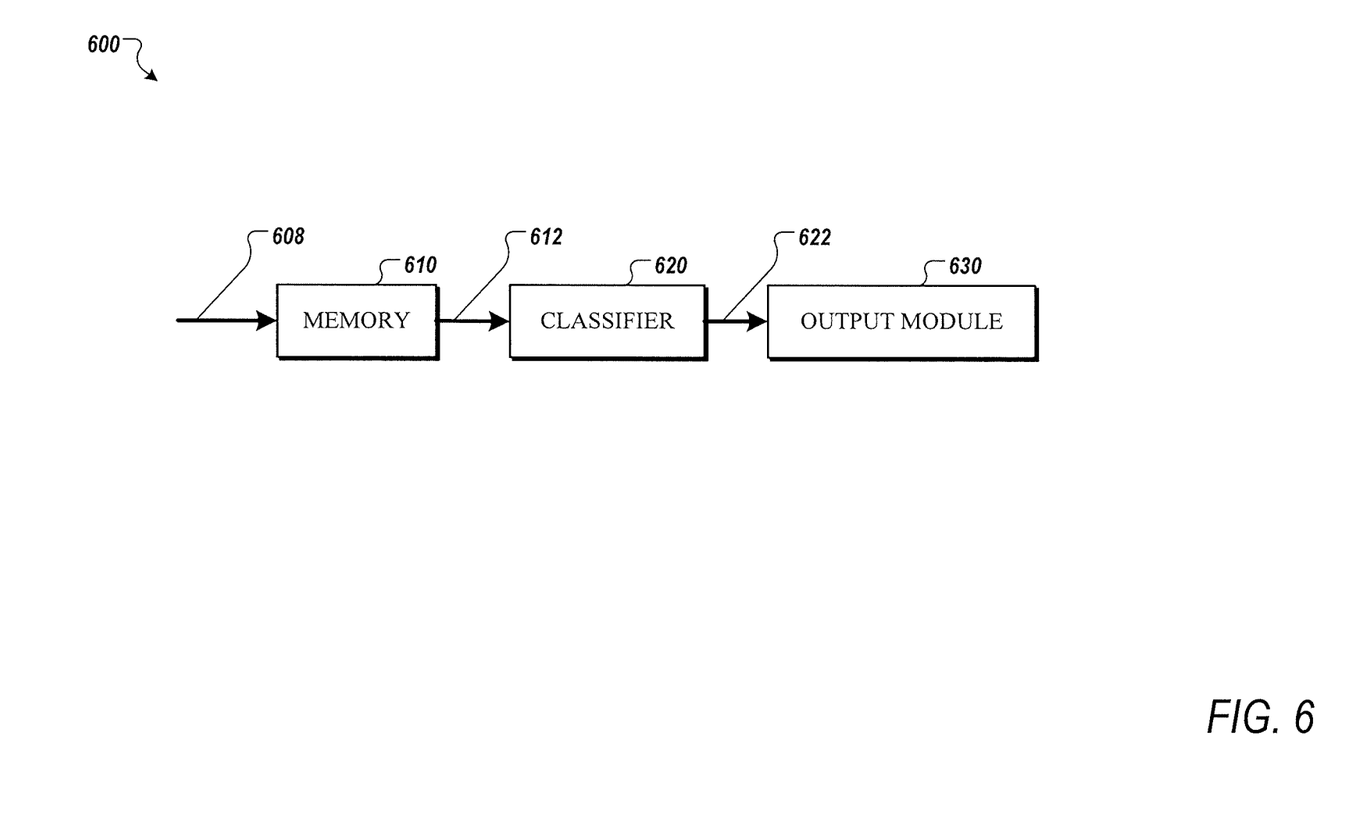
FIG. 6 is a functional block diagram of a diagnosis device according to one or more embodiments of the present disclosure.
Figure 8:
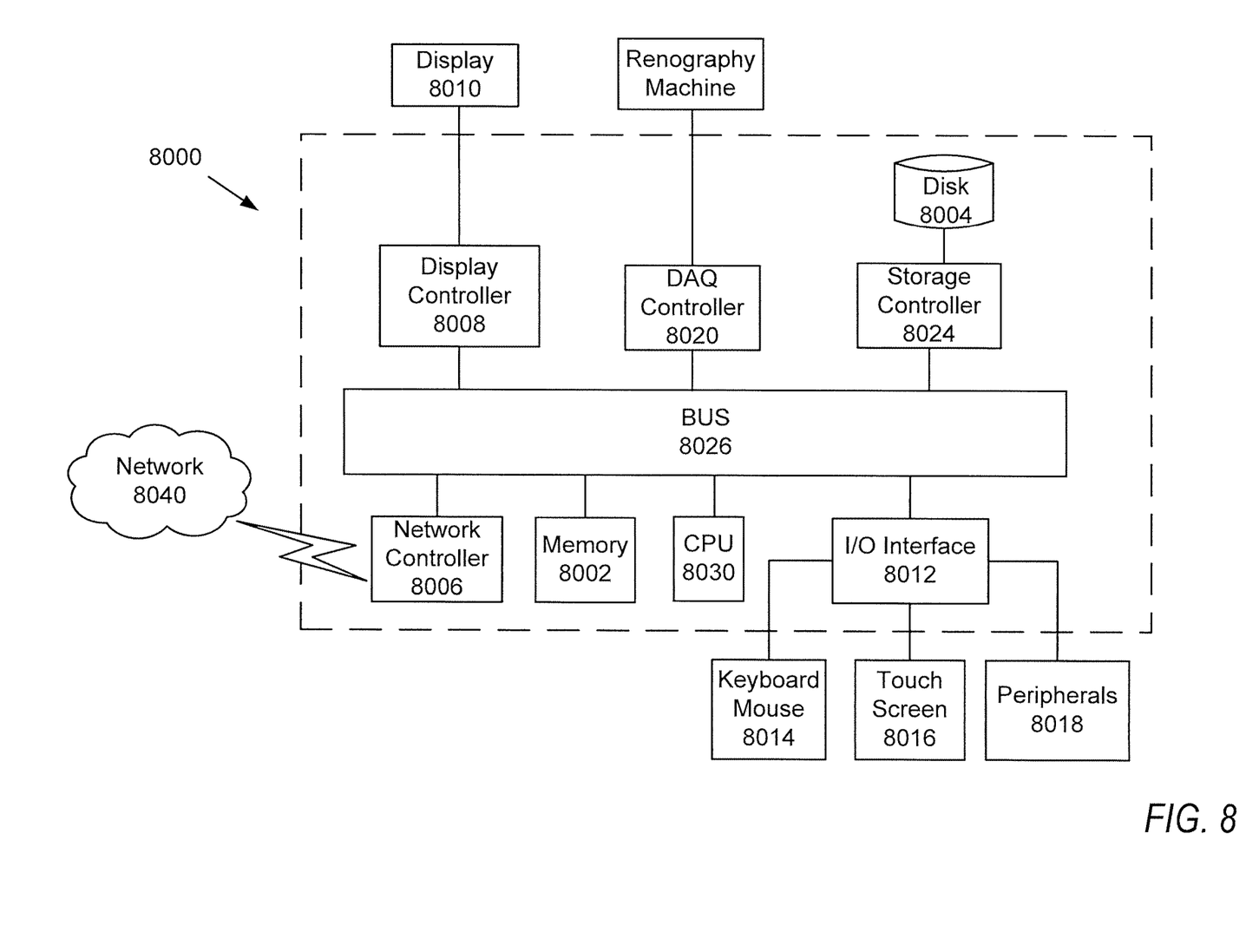
FIG. 8 is a block diagram of a computing device or system according to one or more embodiments of the present disclosure.

Optionally, the linear support vector machine classifier can be implemented by a diagnosis device, such as diagnosis device 600 illustrated in FIG. 6, or a computing device or system, such as computer device or system 8000 as illustrated in in FIG. 8. Further, generating the clinical diagnosis can include subjecting an output signal of a linear support vector machine classifier to a logistic regression function to obtain an approximate probabilistic output corresponding to a probability of a clinically significant renal obstruction representative of part or all of the generated clinical diagnosis 114.

Figure 5:
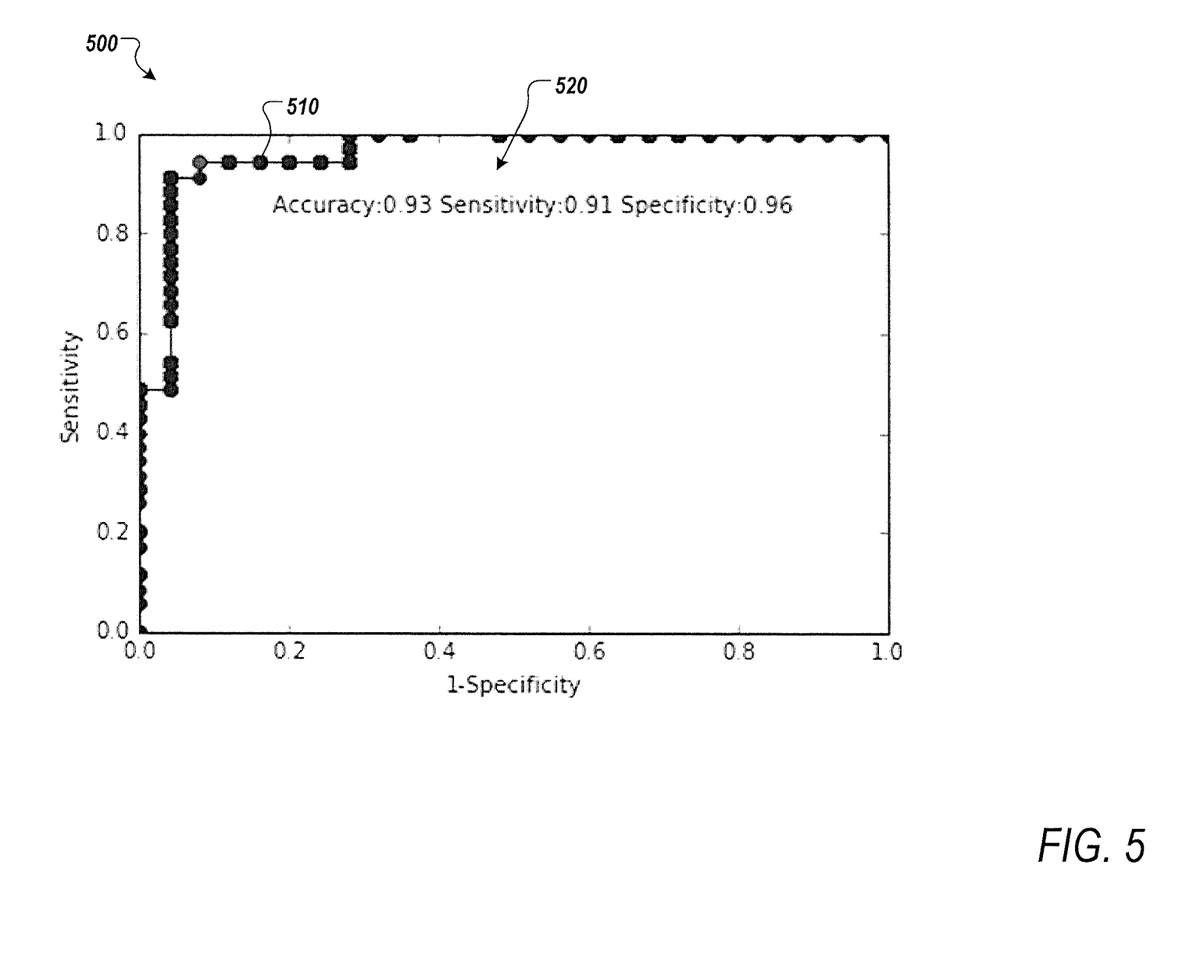
FIG. 5 is a graph showing an example of a receiver operating characteristics curve based on an optimized set of biomarkers according to one or more embodiments of the present disclosure.

FIG. 5 is a graph 500 showing a ROC curve 510 based on an optimal set of biomarkers, according to an exemplary embodiment of the present disclosure. As an example, the curve 510 may result in an accuracy of 0.93, a sensitivity of 0.91, and a specificity of 0.96 520.

At block 116 the method 100 can output the clinical diagnosis. As noted above, the clinical diagnosis can be or include a classification of the renal obstruction, such as critical or non-critical. Further, the output clinical diagnosis can include recommended treatment, such as whether or not surgical intervention is indicated. The clinical diagnosis can be output on a display, such as a graphical user interface of a display device, such as a hand-held portable electronic device or personal computer.

FIG. 6 is a functional block diagram of a diagnosis device 600 according to one or more embodiments of the present disclosure. Optionally, the diagnosis device 600 may be implemented by a computing device or system, such as computer device or system 8000, as illustrated in in FIG. 8.

Generally, diagnosis device 600 can receive an optimized set of biomarkers from a time-activity curve and output a diagnosis of renal obstruction in terms of a classification of the obstruction. Diagnosis device 600 can include a memory 610, a classifier module 620, and an output module 630.

The memory 610 can be configured to receive or to receive and store data corresponding to a set of biomarkers 608 extracted from a time-activity curve of a renograph of a patient, where the set of biomarkers 608 can be based on a previously determined optimized set of biomarkers from a larger group of biomarkers. Optionally, memory 610 may store the previously determined optimized set of biomarkers to control extraction of the set of biomarkers 608 from the time-activity curve.

The trained classifier 620 can receive the subset of the larger set of biomarkers 612 and transform the set of biomarkers to a probabilistic output corresponding to a classification of an obstruction. The classification can be output to the output module 630 in the form of a clinical diagnosis 622 of the obstruction. Further, the clinical diagnosis 622 can include or indicate recommended treatment, such as surgery or no surgery. The clinical diagnosis 622 can be output visually and/or audibly by the output module 630, for instance, to a practitioner or scientist.

Figure 7A:
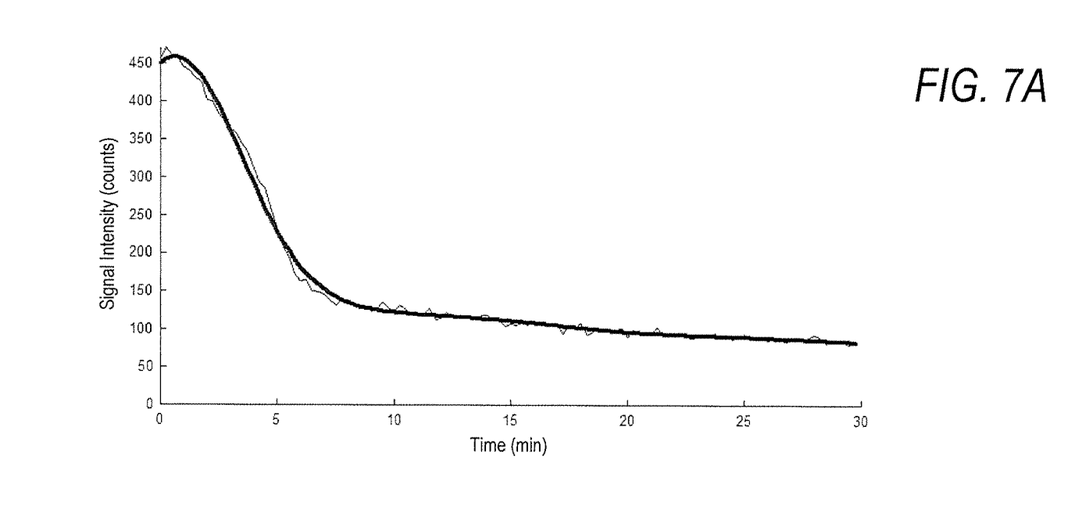
FIG. 7A is a graph showing an example of a time-activity curve (thin line) over time and a noise-minimized time-activity curve (thick line) according to one or more embodiments of the present disclosure.
Figure 7B:
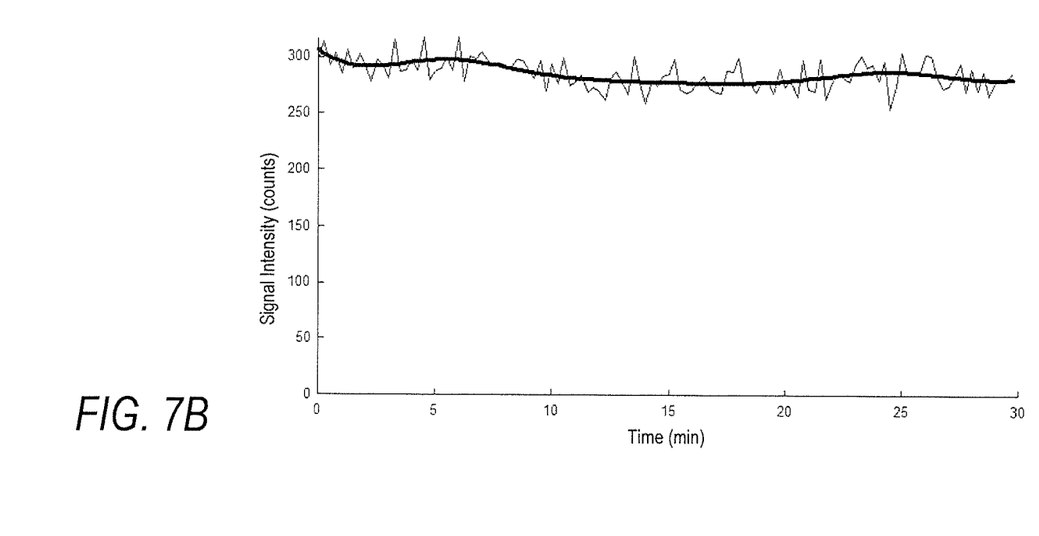
FIG. 7B is a graph showing an example of a time-activity curve (thin line) over time and a noise-minimized time-activity curve (thick line) according to one or more embodiments of the present disclosure.

FIG. 7A and FIG. 7B are implementations of the diagnosis device described in FIG. 6, according to one or more embodiments of the present disclosure. FIG. 7A and FIG. 7B are graphs, with time on the x-axis and counts on the y-axis, illustrating an acquired time-activity curve (thin line) and a noise-minimized time-activity curve (thick line) from which individual biomarkers and sets of biomarkers might be extracted and classified. In an example, only the period of time following administration of a diuretic is evaluated. FIG. 7A is an example of a correctly classified healthy, or unobstructed patient, wherein a noticeable decrease in radiotracer is present 10 minutes after administration of the diuretic. FIG. 7B is an example of a correctly classified diagnosed, or obstructed patient, wherein a noticeable consistency in radiotracer is present 10 minutes after administration of the diuretic. In each case, an optimal operation point, comprising a unique combination of the aforementioned biomarkers, which maximizes the classification accuracy, was employed in the classification of each curve.

Next, a hardware description of a computing device or system 8000 according to exemplary embodiments is described with reference to FIG. 8. Generally speaking, system 8000 can be configured to perform operations to generate and output a clinical diagnosis based on an extracted set of biomarkers as set forth herein, such as according to method 100 in FIG. 1.

In FIG. 8, the computing device 8000 or server includes a CPU 8030 (processing circuitry) which performs the processes described above. The process data and instructions 10 may be stored in memory 8002. These processes and instructions may also be stored on a non-transitory storage medium disk 8004 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device or server communicates, such as another server, computer or database.

Further, a portion of the claimed advancements may be provided as a utility application, background daemon, or component of an operating system, or combination thereof, executing in conjunction with CPU 8030 and an operating system such as Microsoft Windows 7, UNIX, Solaris, LINUX, Apple MAC-OS and other systems known to those skilled in the art.

CPU 8030 may be a Xenon or Core processor from Intel of America or an Opteron processor from AMD of America, or may be other processor types that would be recognized by one of ordinary skill in the art. Alternatively, the CPU 8030 may be implemented on an FPGA, ASIC, PLD or using discrete logic circuits, as one of ordinary skill in the art would recognize. Further, CPU 8030 may be implemented as multiple processors cooperatively working in parallel to perform the instructions of the inventive processes described above.

The computing device or server in FIG. 8 also includes a network controller 8006, such as an Intel Ethernet PRO network interface card from Intel Corporation of America, for interfacing with network 8040. As can be appreciated, the network 8040 can be a public network, such as the Internet, or a private network such as an LAN or WAN network, or any combination thereof and can also include PSTN or ISDN sub-networks. The network 8040 can also be wired, such as an Ethernet network, or can be wireless such as a cellular network including EDGE, 3G and 4G wireless cellular systems. The wireless network can also be Wi-Fi, Bluetooth, or any other wireless form of communication that is known. In an example, the network 8040 can be configured to access a database storing a plurality of mechanical constraints based on the surgical procedure. The network controller 8006 may receive data corresponding to an extracted set of biomarkers.

The computing device or server further includes a display controller 8008, such as a NVIDIA GeForce GTX or Quadro graphics adaptor from NVIDIA Corporation of America for interfacing with display 8010, such as a Hewlett Packard HPL2445w LCD monitor. A general purpose I/O interface 8012 interfaces with a keyboard and/or mouse 8014 as well as a touch screen panel 8016 on or separate from display 8010. General purpose I/O interface also connects to a variety of peripherals 8018 including printers and scanners, such as an OfficeJet or DeskJet from Hewlett Packard.

A data acquisition (DAQ) controller 8020 is also provided in the computing device or server, which may interface to receive data corresponding to an extracted set of biomarkers.

The general purpose storage controller 8024 connects the storage medium disk 8004 with communication bus 8026, which may be an ISA, EISA, VESA, PCI, or similar, for interconnecting all of the components of the computing device or server. In an example, the storage medium disk 8004 can act as a database storing a plurality of mechanical constraints based on the surgical procedure. A description of the general features and functionality of the display 8010, keyboard and/or mouse 8014, as well as the display controller 8008, storage controller 8024, network controller 8006, DAQ controller 8020, and general purpose I/O interface 8012 is omitted herein for brevity as these features are known.

One or more processors can be utilized to implement various functions and/or algorithms described herein, unless explicitly stated otherwise. Additionally, any functions and/or algorithms described herein, unless explicitly stated otherwise, can be performed upon one or more virtual processors, for example on one or more physical computing systems such as a computer farm or a cloud drive.

Reference has been made to flowchart illustrations and block diagrams of methods, systems and computer program products according to implementations of this disclosure. Aspects thereof are implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks. Moreover, the present disclosure is not limited to the specific circuit elements described herein, nor is the present disclosure limited to the specific sizing and classification of these elements.

Embodiments of the present disclosure may also be as set forth in the following parentheticals.

(1) A method for detecting a clinically significant renal obstruction, the method comprising: receiving, via processing circuitry, data corresponding to one or more time-activity curves, each of the one or more time-activity curves being associated with a medical image corresponding to a kidney of a patient; extracting, via the processing circuitry, one or more biomarkers from the one or more time-activity curves; and classifying, via the processing circuitry, the one or more time-activity curves according to the one or more extracted biomarkers of the one or more time-activity curves.

(2) The method according to (1), wherein the medical image of the kidney of the patient is a renograph of the patient.

(3) The method according to either (1) or (2), wherein the classifying comprises: classifying the one or more time-activity curves according to the one or more extracted biomarkers of the one or more time-activity curves based upon a classifier, wherein the classifier is selected from a group of classifiers, each one of the group of classifiers being trained on a dataset, each dataset being a subset of a reference database including a corpus of labeled reference time-activity curves, each labeled reference time-activity curve comprising one or more biomarkers associated in the database with a corresponding text description of the one or more biomarkers, wherein each dataset comprises a unique combination of the one or more biomarkers of each of the labeled reference time-activity curves of the corpus of labeled reference time-activity curves, wherein a receiver characteristics curve is generated for an output of each one of the group of trained classifiers, wherein the selected classifier is selected from the group of trained classifiers based upon the receiver characteristics curve generated for the output of each one of the group of trained classifiers, wherein the unique combination of one or more biomarkers associated with the selected classifier corresponds to the one or more extracted biomarkers from the one or more time-activity curves.

(4) The method according to any of (1) to (3), wherein the selected classifier maximizes an area under the receiver characteristics curve, compared with the area under the receiver characteristics curve for each of the one or more receiver characteristics curves generated from the output of each one of the group of trained classifiers.

(5) The method according to any of (1) to (4), wherein the classifier comprises a linear support vector machine classifier.

(6) The method according to any of (1) to (5), wherein the output of the linear support vector machine classifier is an input of a logistic regression function.

(7) The method according to any of (1) to (6), wherein an output of the logistic regression function is an approximate probabilistic output.

(8) The method according to any of (1) to (7), wherein classification of the one or more time-activity curves according to the one or more extracted biomarkers of the one or more time-activity curves is based upon a comparison of the approximate probabilistic output of the logistic regression function and a pre-determined classification threshold.

(9) The method according to any of (1) to (8), wherein the selected classifier maximizes an area under the receiver characteristics curve, compared with the area under the receiver characteristics curve for each of the one or more receiver characteristics curves generated from the output of each one of the group of trained classifiers.

(10) The method according to any of (1) to (9), wherein the output of the logistic regression function is a measure of confidence in the accuracy of the output of the linear support vector machine classifier.

(11) The method according to any of (1) to (10), wherein the unique combination of one or more biomarkers includes at least one of a percentage of clearance of a radiotracer from a kidney of the patient after a pre-determined time, half-time ($t\frac{1}{2}$) to drain the radiotracer from the kidney after administration of a diuretic, mean slope of the one or more time-activity curves at one or more pre-determined time intervals, moments of the one or more time-activity curves, length of the one or more time-activity curves, curve shape, Fourier transform coefficients, wavelet analysis coefficients, maximum value, and minimum value.

(12) An apparatus for detecting a clinically significant renal obstruction, the method comprising processing circuitry configured to: receive data corresponding to one or more time-activity curves, each of the one or more time-activity curves being associated with a medical image corresponding to a kidney of a patient; extract one or more biomarkers from the one or more time-activity curves; and classify the one or more time-activity curves according to the one or more extracted biomarkers of the one or more time-activity curves.

(13) The apparatus according to (12), wherein the processing circuity is further configured to: classify the one or more time-activity curves according to the one or more extracted biomarkers of the one or more time-activity curves based upon a classifier, wherein the classifier is selected from a group of classifiers, each one of the group of classifiers being trained on a dataset, each dataset being a subset of a reference database including a corpus of labeled reference time-activity curves, each labeled reference time-activity curve comprising one or more biomarkers associated in the database with a corresponding text description of the one or more biomarkers, wherein each dataset comprises a unique combination of the one or more biomarkers of each of the labeled reference time-activity curves of the corpus of labeled reference time-activity curves, wherein a receiver characteristics curve is generated for an output of each one of the group of trained classifiers, wherein the selected classifier is selected from the group of trained classifiers based upon the receiver characteristics curve generated for the output of each one of the group of trained classifiers, wherein the unique combination of one or more biomarkers associated with the selected classifier corresponds to the one or more extracted biomarkers from the one or more time-activity curves.

(14) The apparatus according to either (12) or (13), wherein the selected classifier maximizes an area under the receiver characteristics curve, compared with the area under the receiver characteristics curve for each of the one or more receiver characteristics curves generated from the output of each one of the group of trained classifiers.

(15) The apparatus according to any of (12) to (14), wherein the classifier comprises a linear support vector machine classifier.

(16) The apparatus according to any of (12) to (15), wherein the output of the linear support vector machine classifier is an input of a logistic regression function.

(17) The apparatus according to any of (12) to (16), wherein an output of the logistic regression function is an approximate probabilistic output.

(18) The apparatus according to any of (12) to (17), wherein classification of the one or more time-activity curves according to the one or more extracted biomarkers of the one or more time-activity curves is based upon a comparison of the approximate probabilistic output of the logistic regression function and a pre-determined classification threshold.

(19) The apparatus according to any of (12) to (18), wherein the selected classifier maximizes an area under the receiver characteristics curve, compared with the area under the receiver characteristics curve for each of the one or more receiver characteristics curves generated from the output of each one of the group of trained classifiers.

(20) The apparatus according to any of (12) to (19), wherein the output of the logistic regression function is a measure of confidence in the accuracy of the output of the linear support vector machine classifier.

(21) The apparatus according to any of (12) to (20), wherein the unique combination of one or more biomarkers includes at least one of a percentage of clearance of a radiotracer from a kidney of the patient after a pre-determined time, half-time ($t\frac{1}{2}$) to drain the radiotracer from the kidney after administration of a diuretic, mean slope of the one or more time-activity curves at one or more pre-determined time intervals, moments of the one or more time-activity curves, length of the one or more time-activity curves, curve shape, Fourier transform coefficients, wavelet analysis coefficients, maximum value, and minimum value.

(22) A non-transitory computer readable medium having stored thereon a program that when executed by the computer causes the computer to implement a method for detecting a clinically significant renal obstruction, the method comprising: receiving, via processing circuitry, data corresponding to one or more time-activity curves, each of the one or more time-activity curves being associated with a medical image corresponding to a kidney of a patient; extracting, via the processing circuitry, one or more biomarkers from the one or more time-activity curves; and classifying, via the processing circuitry, the one or more time-activity curves according to the one or more extracted biomarkers of the one or more time-activity curves.

(23) A method for diagnosis of a clinically significant renal obstruction in a patient using signal analysis and machine learning, the method comprising: receiving, using processing circuitry, data corresponding to a machine learned set of extracted biomarkers from one or more time-activity curves associated with a renogram of the patient; and generating, using the processing circuitry, a clinical diagnosis based on the machine learned set of extracted biomarkers.

(24) The method of (23), wherein the clinically significant renal obstruction is Ureteropelvic Junction Obstruction (UPJO).

(25) The method of (23), further comprising outputting, using the processing circuitry, data corresponding to the generated clinical diagnosis for output on a user interface of an electronic device.

(26) The method of (25), wherein the user interface is a graphical user interface (GUI), and the electronic device is a hand-held portable electronic device.

(27) The method of (23), wherein the machine learned set of biomarkers includes at least a percentage of clearance of a radiotracer from a kidney of the patient after a specified time and/or half-time ($t\frac{1}{2}$) to drain the radiotracer from the kidney after administration of diuretic.

(28) The method of (23), wherein the machine learned set of biomarkers includes the combination of any of the following: a percentage of clearance of a radiotracer from a kidney of the patient after a specified time, half-time ($t\frac{1}{2}$) to drain the radiotracer from the kidney after administration of diuretic, mean slope of the one or more time-activity curves at one or more pre-determined time intervals, moments of the one or more time-activity curves, and length of the one or more time-activity curves.

(29) The method of (23), wherein the machine learned set of biomarkers consists of a percentage of clearance of a radiotracer from a kidney of the patient at a specified time, mean slope of the one or more time-activity curves at one or more pre-determined time intervals, moments of the one or more time-activity curves, and length of the one or more time-activity curves.

(30) The method of (23), further comprising extracting the machine learned set biomarkers from one or more time-activity curves associated with the renogram of the patient.

(31) The method of (30), wherein the machine learned set of biomarkers is an optimized group of biomarkers selected from a larger group of biomarkers extracted from the one or more time-activity curves.

(32) The method of (31), wherein the larger group of biomarkers were extracted based on curve shape of the one or more time-activity curves and/or Fourier/wavelet analysis of the one or more time-activity curves.

(33) The method of (31), wherein the larger group of biomarkers were extracted for the one or more time-activity curves based on maximum and minimum values and Fourier transform and wavelet analysis coefficients.

(34) The method of (23), further comprising performing renography and/or functional magnetic resonance urography (fMRU) on one or both kidneys of the patient to obtain the renogram of the patient.

(35) The method of (23), wherein said generating the clinical diagnosis is based on weight coefficients for the machine learned set of extracted biomarkers.

(36) The method of (23), further comprising performing diuresis renography (DR) and/or functional magnetic resonance urography (fMRU) on one or both kidneys of the patient to obtain the renogram of the patient.

(37) The method of (36), wherein classification of renal obstruction is performed using a linear support vector machine classifier.

(38) The method of (36), wherein the classification of renal obstruction is one of non-operative and surgical.

(39) The method of (23), wherein the biomarkers of the machine learned set of biomarkers are selected based on a maximized area under a receiver operating characteristics (ROC) curve determination.

(40) The method of (39), wherein the analysis is performed using a linear support vector machine classifier.

(41) The method of (39), wherein the generated clinical diagnosis is a binary decision.

(42) The method of (23), wherein the generated clinical diagnosis is a probability of a clinically significant renal obstruction.

(43) The method of (23), wherein the generated clinical diagnosis is an approximate probabilistic output generated based on an output of a linear support vector machine classifier processed by a logistic regression function.

(44) The method of (23), wherein said generating the clinical diagnosis includes subjecting an output signal of a linear support vector machine classifier to a logistic regression function to obtain an approximate probabilistic output corresponding to a probability of a clinically significant renal obstruction representative of part or all of the generated clinical diagnosis.

(45) The method of (23), wherein said generating the clinical diagnosis is responsive to receiving one or more of said time-activity curves associated with only one renogram.

(46) The method of (23), wherein said generating the clinical diagnosis is responsive to receiving only said one or more renograms.

(47) A non-transitory computer-readable storage medium storing computer-readable instructions that, when executed by a computer, cause the computer to perform a method according to any one of (23) to (46).

(48) A system for classifying ureteropelvic junction obstruction (UPJO) comprising: memory; and a processor operatively connected to the memory, the processing being configured to: extract a set of biomarkers from a time-activity curve corresponding to a renogram of a patient, the extracted set of biomarkers corresponding to a predetermined set of machine-learned biomarkers stored in the memory, and determine, based on the extracted set of biomarkers, a probability or determination of critical UPJO for clinical diagnosis of UPJO in the patient.

(49) The system of (48), further comprising a display device configured to display the probability and/or determination of critical UPJO and/or the recommended treatment.

(50) The system of (49), wherein the processor is configured to control display on the display device of a graphical user interface (GUI) configured to display the probability and/or determination of critical UPJO and/or the recommended treatment.

(51) The system of (48), wherein the predetermined set of machine-learned biomarkers includes a combination of a percentage of clearance of a radiotracer from a kidney of the patient at a specified time and half-time (VA) to drain the radiotracer from the kidney after administration of diuretic.

(52) The system of (48), wherein the predetermined set of machine-learned biomarkers includes any combination of a percentage of clearance of a radiotracer from a kidney of the patient at a specified time, half-time ($t\frac{1}{2}$) to drain the radiotracer from the kidney after administration of diuretic, mean slope of the one or more time-activity curves at one or more pre-determined time intervals, moments of the one or more time-activity curves, and length of the one or more time-activity curves.

(53) The system of (48), wherein the predetermined set of machine-learned biomarkers consists of a percentage of clearance of a radiotracer from a kidney of the patient at a specified time, mean slope of the one or more time-activity curves during the first five minutes, mean slope of the one or more time-activity curves between 15 and 20 minutes, moment of the one or more time-activity curves of order 4, and length of the one or more time-activity curves.

(54) The system of (48), wherein the predetermined set of machine-learned biomarkers is an optimized group of biomarkers selected from a larger group of biomarkers extracted from one or more previous time-activity curves.

(55) The system of (54), wherein the one or more previous time-activity curves are from one or more patients other than said patient.

(56) The system of (48), wherein classification is performed using a linear support vector machine classifier of the processor.

(57) The system of (48), wherein the probability or determination of critical UPJO correlates to a classification of UPJO in terms of critical UPJO requiring surgical treatment or non-critical UPJO not requiring surgical treatment.

(58) The system of (48), wherein the probability or determination of critical UPJO is responsive to receiving one or more time-activity curves associated with the patient.

(59) The system of (48), wherein the probability or determination of critical UPJO is based on one or more of said renograms.

(60) The system of (48), further comprising output data corresponding to a recommended treatment based on the determined probability of critical UPJO.

(61) The method according to (48), wherein the medical image of the kidney of the patient is a renograph of the patient.

Having now described embodiments of the present disclosure, it should be apparent to those skilled in the art that the foregoing is merely illustrative and not limiting, having been presented by way of example only. Thus, although particular configurations have been discussed and illustrated herein, other configurations can be and are also employed. Further, numerous modifications and other embodiments (e.g., combinations, rearrangements, etc.) are enabled by the present disclosure and are contemplated as falling within the scope of the present disclosure and any equivalents thereto. Features of the disclosed embodiments can be combined, rearranged, omitted, etc., within the scope of described subject matter to produce additional embodiments. Furthermore, certain features may sometimes be used to advantage without a corresponding use of other features. Accordingly, Applicant(s) intend(s) to embrace all such alternatives, modifications, equivalents, and variations that are within the spirit and scope of the present disclosure.

The invention claimed is:

1. A method for detecting a clinically significant renal obstruction, the method comprising:
receiving, via processing circuitry, data corresponding to one or more time-activity curves, each of the one or more time-activity curves being associated with a medical image corresponding to a kidney of a patient;
extracting, via the processing circuitry, one or more biomarkers from the one or more time-activity curves, the one or more biomarkers corresponding to a predetermined set of machine-learned biomarkers stored in memory; and
classifying, via the processing circuitry, the one or more time-activity curves according to the one or more extracted biomarkers of the one or more time-activity curves based on a classifier,
wherein the classifier is selected from a group of classifiers, each one of the group of classifiers being trained on a dataset, each dataset being a subset of a reference database including a corpus of labeled reference time-activity curves, each labeled reference time-activity curve including one or more biomarkers associated in the database,
wherein each dataset includes a unique combination of the one or more biomarkers of each of the labeled reference time-activity curves of the corpus of labeled reference time-activity curves, the classifier being selected based on a receiver characteristics curve that is generated for a classification output of each one of the group of classifiers, the receiver characteristics curve including a false positive rate and a true positive rate for classification by each one of the group of classifiers based on the unique combination of the one or more biomarkers;
the predetermined set of machine-learned biomarkers being based on the dataset used for training of the selected classifier.

2. The method according to claim 1, wherein the medical image of the kidney of the patient is a renograph of the patient.

3. The method according to claim 1,
wherein the unique combination of the one or more biomarkers associated with the selected classifier corresponds to the one or more extracted biomarkers from the one or more time-activity curves.

4. The method according to claim 3, wherein the selected classifier maximizes an area under the receiver characteristics curve, compared with the area under the receiver characteristics curve for each of the one or more receiver characteristics curves generated from the output of each one of the group of trained classifiers.

5. The method according to claim 3, wherein the classifier comprises a linear support vector machine classifier.

6. The method according to claim 5, wherein the output of the linear support vector machine classifier is an input of a logistic regression function.

7. The method according to claim 6, wherein an output of the logistic regression function is an approximate probabilistic output.

8. The method according to claim 7, wherein classification of the one or more time-activity curves according to the one or more extracted biomarkers of the one or more time-activity curves is based upon a comparison of the approximate probabilistic output of the logistic regression function and a pre-determined classification threshold.

9. The method according to claim 8, wherein the selected classifier maximizes an area under the receiver characteristics curve, compared with the area under the receiver characteristics curve for each of the one or more receiver characteristics curves generated from the output of each one of the group of trained classifiers.

10. The method according to claim 8, wherein the output of the logistic regression function is a measure of confidence in the accuracy of the output of the linear support vector machine classifier.

11. The method according to claim 3, wherein the unique combination of one or more biomarkers includes at least one of a percentage of clearance of a radiotracer from a kidney of the patient after a pre-determined time, half-time (t½) to drain the radiotracer from the kidney after administration of a diuretic, mean slope of the one or more time-activity curves at one or more pre-determined time intervals, moments of the one or more time-activity curves, length of the one or more time-activity curves, curve shape, Fourier transform coefficients, wavelet analysis coefficients, maximum value, and minimum value.

12. An apparatus for detecting a clinically significant renal obstruction comprising:
processing circuitry configured to:
receive data corresponding to one or more time-activity curves, each of the one or more time-activity curves being associated with a medical image corresponding to a kidney of a patient;
extract one or more biomarkers from the one or more time-activity curves, the one or more biomarkers corresponding to a predetermined set of machine-learned biomarkers stored in memory; and
classify the one or more time-activity curves according to the one or more extracted biomarkers of the one or more time-activity curves based on a classifier,
wherein the classifier is selected from a group of classifiers, each one of the group of classifiers being trained on a dataset, each dataset being a subset of a reference database including a corpus of labeled reference time-activity curves, each labeled reference time-activity curve including one or more biomarkers associated in the database,
wherein each dataset includes a unique combination of the one or more biomarkers of each of the labeled reference time-activity curves of the corpus of labeled reference time-activity curves, the classifier being selected based on a receiver characteristics curve that is generated for a classification output of each one of the group of classifiers, the receiver characteristics curve including a false positive rate and a true positive rate for classification hy each one of the group of classifiers based on the unique combination of the one or more biomarkers,
the predetermined set of machine-learned biomarkers being based on the dataset used for training of the selected classifier.

13. The apparatus according to claim 12,
wherein the unique combination of the one or more biomarkers associated with the selected classifier corresponds to the one or more extracted biomarkers from the one or more time-activity curves.

14. The apparatus according to claim 13, wherein the selected classifier maximizes an area under the receiver characteristics curve, compared with the area under the receiver characteristics curve for each of the one or more receiver characteristics curves generated from the output of each one of the group of trained classifiers.

15. The apparatus according to claim 14, wherein the classifier comprises a linear support vector machine classifier.

16. The apparatus according to claim 15, wherein the output of the linear support vector machine classifier is an input of a logistic regression function.

17. The apparatus according to claim 16, wherein an output of the logistic regression function is an approximate probabilistic output.

18. The apparatus according to claim 17, wherein classification of the one or more time-activity curves according to the one or more extracted biomarkers of the one or more time-activity curves is based upon a comparison of the approximate probabilistic output of the logistic regression function and a pre-determined classification threshold.

19. The apparatus according to claim 17, wherein the selected classifier maximizes an area under the receiver characteristics curve, compared with the area under the receiver characteristics curve for each of the one or more receiver characteristics curves generated from the output of each one of the group of trained classifiers.

20. The apparatus according to claim 18, wherein the output of the logistic regression function is a measure of confidence in the accuracy of the output of the linear support vector machine classifier.

21. The apparatus according to claim 13, wherein the unique combination of one or more biomarkers includes at least one of a percentage of clearance of a radiotracer from a kidney of the patient after a pre-determined time, half-time (t½) to drain the radiotracer from the kidney after administration of a diuretic, mean slope of the one or more time-activity curves at one or more pre-determined time intervals, moments of the one or more time-activity curves, length of the one or more time-activity curves, curve shape, Fourier transform coefficients, wavelet analysis coefficients, maximum value, and minimum value.

22. A non-transitory computer readable medium having stored thereon a program that when executed by the computer causes the computer to implement a method for detecting a clinically significant renal obstruction, the method comprising:
  receiving, via processing circuitry, data corresponding to one or more time-activity curves, each of the one or more time-activity curves being associated with a medical image corresponding to a kidney of a patient;
  extracting, via the processing circuitry, one or more biomarkers from the one or more time-activity curves, the one or more biomarkers corresponding to a predetermined set of machine-learned biomarkers stored in memory; and
  classifying, via the processing circuitry, the one or more time-activity curves according to the one or more extracted biomarkers of the one or more time-activity curves based on a classifier,
  wherein the classifier is selected from a group of classifiers, each one of the group of classifiers being trained on a dataset, each dataset being a subset of a reference database including a corpus of labeled reference time-activity curves, each labeled reference time-activity curve including one or more biomarkers associated in the database,
  wherein each dataset includes a unique combination of the one or more biomarkers of each of the labeled reference time-activity curves of the corpus of labeled reference time-activity curves, the classifier being selected based on a receiver characteristics curve that is generated for a classification output of each one of the group of classifiers, the receiver characteristics curve including a false positive rate and a true positive rate for classification hy each one of the group of classifiers based on the unique combination of the one or more biomarkers,
  the predetermined set of machine-learned biomarkers being based on the dataset used for training of the selected classifier.

* * * * *